United States Patent
DeLuca et al.

(10) Patent No.: US 6,844,331 B2
(45) Date of Patent: Jan. 18, 2005

(54) (20S)-1α-HYDROXY-2α-METHYL AND 2β-METHYL-19-NOR-VITAMIN $D_3$ AND THEIR USES

(75) Inventors: Hector F. DeLuca, Deerfield, WI (US); Rafal R. Sicinski, Warsaw (PL); Pawel K. Grzywacz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/762,906

(22) Filed: Jan. 22, 2004

(65) Prior Publication Data

US 2004/0152677 A1 Aug. 5, 2004

Related U.S. Application Data

(62) Division of application No. 10/127,180, filed on Apr. 22, 2002.

(51) Int. Cl.⁷ .................. C07C 401/00; A61K 31/59
(52) U.S. Cl. ..................... 514/167; 552/653
(58) Field of Search .................. 514/167; 552/653

(56) References Cited

U.S. PATENT DOCUMENTS

| | | | | | |
|---|---|---|---|---|---|
| 5,391,755 | A | * | 2/1995 | DeLuca et al. | 548/110 |
| 5,581,006 | A | * | 12/1996 | DeLuca et al. | 556/405 |
| 5,945,410 | A | * | 8/1999 | DeLuca et al. | 514/167 |
| 6,127,559 | A | * | 10/2000 | DeLuca et al. | 552/653 |
| 6,306,844 | B1 | | 10/2001 | DeLuca et al. | |
| 6,667,298 | B2 | * | 12/2003 | DeLuca et al. | 514/167 |
| 6,683,219 | B2 | * | 1/2004 | DeLuca et al. | 568/15 |

OTHER PUBLICATIONS

Sicinski et al, "New 1Alpha–25–Dihydroxy–19–Norvitamin D3 Compounds of High Biological Activity: Synthesis and Biological Evaluation of 2–Hydroxymethyl, 2–Methyl, and 2–Methylene Analogues," Journal of Medicinal Chemistry, American Chemical Society, Oct. 22, 1998, pp. 4662–4674, vol. 41, XP002105465.

Bouillon et al, "Stucture–Function Relationships in the Vitamin D Endocrine System," Endocrine Reviews, Apr. 1995, pp. 200–257, vol. 16, No. 2, XP002247361.

Castedo et al, Palladium–Catalyzed Synthesis of Dienynes Related to Vitamin D from Enol Triflates, Tetrahedron Letters, 1986, pp. 1523–1526, vol. 27, No. 13, XP009013726.

* cited by examiner

*Primary Examiner*—Sabiha N. Qazi
(74) *Attorney, Agent, or Firm*—Andrus, Sceales, Starke & Sawall, LLP

(57) ABSTRACT

This invention discloses (20S)-1α-hydroxy-2α-methyl-19-nor-vitamin $D_3$ and (20S)-1α-hydroxy-2β-methyl-19-nor-vitamin $D_3$ and pharmaceutical uses therefor. These compounds exhibit pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. These compounds also have very significant calcemic activity and therefore may be used to treat immune disorders in humans as well as metabolic bone diseases such as osteoporosis.

5 Claims, 1 Drawing Sheet

(20S)-1α-HYDROXY-2α-METHYL AND 2β-METHYL-19-NOR-VITAMIN D₃ AND THEIR USES

CROSS-REFERENCE TO RELATED APPLICATION

The present application is a divisional of copending U.S. patent application Ser. No. 10/127,180 filed Apr. 22, 2002.

BACKGROUND OF THE INVENTION

This invention relates to vitamin D compounds, and more particularly to the pro-drugs (20S)-1α-hydroxy-2α-methyl and 2β-methyl-19-nor-vitamin D₃ and their pharmaceutical uses.

The natural hormone, 1α,25-dihydroxyvitamin D₃ and its analog in ergosterol series, i.e. 1α,25-dihydroxyvitamin D₂ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin D₃, 1α-hydroxyvitamin D₂, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin D₃) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin D₃ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin D₃ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-nor-vitamin D₃ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, two analogs which are characterized by the presence of a methyl substituent at the carbon 2 (C-2) and the absence of a hydroxyl group at carbon 25 (C-25) in the side chain have been synthesized and tested. These two analogs are characterized by a hydroxyl group at carbon 1 and a vitamin D₃ side chain with the methyl group attached to carbon 20 in the unnatural or epi orientation, i.e. (20S)-1α-hydroxy-2α-methyl and 2β-methyl-19-nor-vitamin D₃. These vitamin D analogs seemed interesting targets because the relatively small methyl group at C-2 should not interfere with the vitamin D receptor. Moreover, molecular mechanics studies seem to indicate that such molecular modification substantially alters the conformation of the cyclohexanediol ring A, shifting its conformational equilibrium toward the chair form with equatorially oriented methyl substituent at C-2.

SUMMARY OF THE INVENTION

The present invention is directed toward the pro-drugs (20S)-1α-hydroxy-2α-methyl-19-nor-vitamin D₃ (formula Ia below) and (20S)-1α-hydroxy-2β-methyl-19-nor-vitamin D₃ (formula Ib below), their biological activity, and various pharmaceutical uses for these compounds.

Structurally these 2α-methyl and 2β-methyl 19-nor analogs are characterized by formula Ia and Ib, respectively shown below:

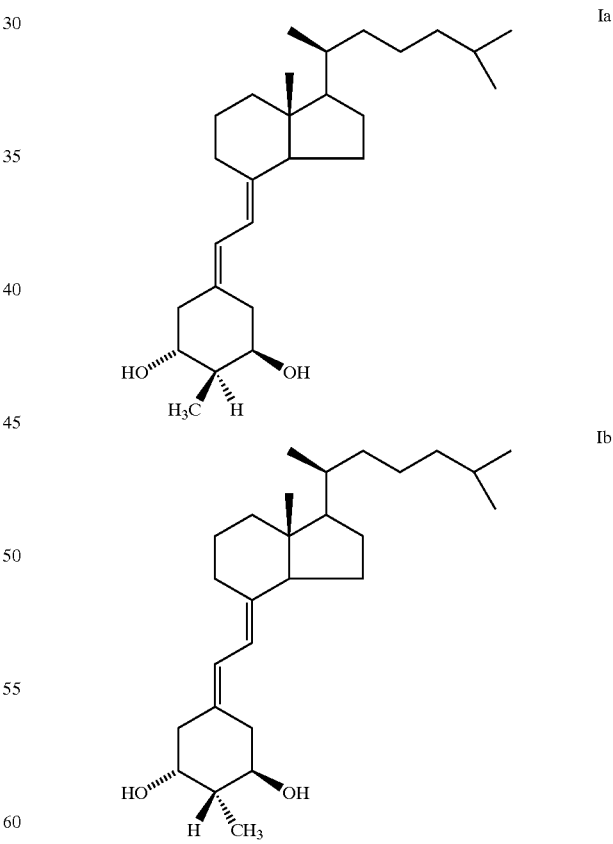

The above two compounds exhibit a desired, and highly advantageous, pattern of biological activity. These compounds do not bind or bind poorly to the vitamin D receptor. However, the 2α-methyl compound has greater intestinal calcium transport activity, as compared to that of 1α,25- dihydroxyvitamin $D_3$, and has greater ability to mobilize calcium from bone, as compared to $1\alpha,25$-dihydroxyvitamin $D_3$. The $2\beta$-methyl compound has intestinal calcium transport activity and bone calcium mobilization activity about the same as $1\alpha,25$-dihydroxyvitamin $D_3$. Hence, these compounds can be characterized as having very potent calcemic activity, and are highly specific in their calcemic activity. Their activity on mobilizing calcium from bone and either high or normal intestinal calcium transport activity allows the in vivo administration of these compounds for the treatment of metabolic bone diseases where bone loss is a major concern. Because of their activity on bone, these compounds would be preferred therapeutic agents for the treatment of diseases where bone formation is desired, such as osteoporosis, especially low bone turnover osteoporosis, steroid induced osteoporosis, senile osteoporosis or postmenopausal osteoporosis, as well as osteomalacia.

The compounds of the invention have also been discovered to be especially suited for treatment and prophylaxis of human disorders which are characterized by an imbalance in the immune system, e.g. in autoimmune diseases, including multiple sclerosis, lupis, diabetes mellitus, host versus graft reaction, and rejection of organ transplants; and additionally for the treatment of inflammatory diseases, such as rheumatoid arthritis, asthma, and inflammatory bowel diseases such as celiac disease and Crohns disease. Acne, alopecia and hypertension are other conditions which may be treated with the compounds of the invention.

The above compounds are also characterized by high or significant cell differentiation activity. Thus, these compounds also provide a therapeutic agent for the treatment of psoriasis, or as an anti-cancer agent, especially against leukemia, colon cancer, breast cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds may be present in a composition to treat the above-noted diseases and disorders in an amount from about 0.01 μg/gm to about 100 μg/gm of the composition, and may be administered topically, transdermally, orally or parenterally in dosages of from about 0.01 μg/day to about 100 μg/day.

Figure 1:
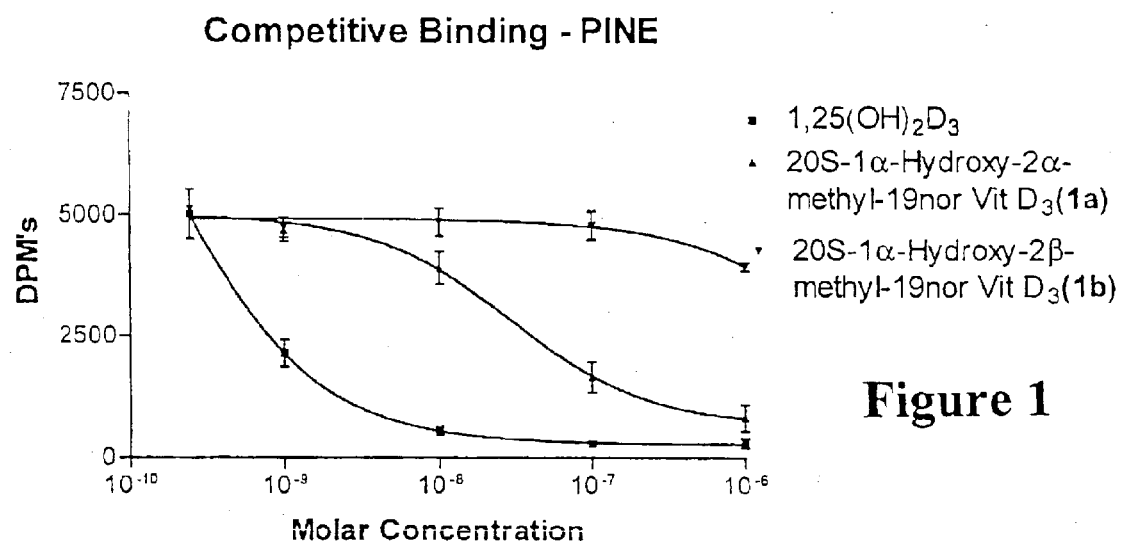
FIG. 1 is a graph illustrating the relative activity of (20S)-1α-hydroxy-2α-methyl-19-nor-vitamin $D_3$, (20S)-1α-hydroxy-2β-methyl-19-nor-vitamin $D_3$, and 1α,25-dihydroxyvitamin $D_3$ to compete for binding of [$^3$H]-1,25-(OH)$_2$-$D_3$ to the vitamin D pig intestinal nuclear receptor.

DETAILED DESCRIPTION OF THE INVENTION (20S)-1α-Hydroxy-2α-methyl-19-nor-vitamin $D_3$ and (20S)-1α-hydroxy-2β-methyl-19-nor-vitamin $D_3$ were synthesized and tested. Structurally, these 19-nor analogs are characterized by the formula Ia and Ib, respectively, previously illustrated herein.

The preparation of (20S)-1α-hydroxy-2α-methyl- and (20S)-1α-hydroxy-2β-methyl-19-nor-vitamin $D_3$ having structures Ia and Ib can be accomplished by a common general method, i.e. the condensation of a bicyclic Windaus-Grundmann type ketone II with the allylic phosphine oxide III to the corresponding 2-methylene-19-nor-vitamin D analog IV followed by deprotection of hydroxyls at C-1 and C-3 in the latter compound; and then followed by a selective reduction of the exomethylene group at C-2 in compound V to provide the 2α-methyl isomer (Ia) and 2β-methyl isomer (Ib):

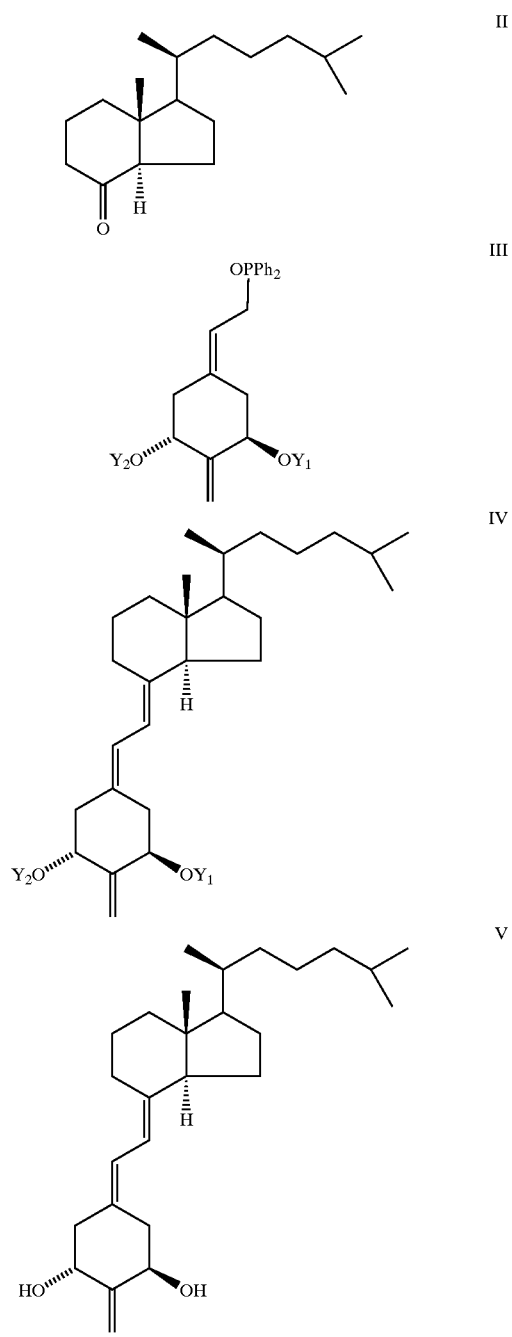

In the structures III and IV groups $Y_1$ and $Y_2$ are hydroxy-protecting groups, preferably tBuMe$_2$Si groups, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414(1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

A hydrindanone of the structure II is a new compound that can be prepared from commercial vitamin $D_2$ by modification of known methods. Thus, the starting alcohol 1 was prepared from commercial vitamin $D_2$ in 3 steps (Scheme 1). The resulting C-22 alcohol 1 was oxidized to the aldehyde 2, which then was equilibrated at C-20. The mixture of (20R)- and (20S)-aldehydes was reduced and (20R)-alcohol 3 was isolated by chromatography. This, in turn, was tosylated and the tosylate 4 coupled with the Grignard reagent 5 in the presence of dilithium tetrachlorocuprate. The obtained hydrindanol 6 was oxidized to the new (20S)-Grundmann ketone analog II.

For the preparation of the required phosphine oxides of general structure III, a new synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The final step of the process is the selective homogeneous catalytic hydrogenation of the exomethylene unit at carbon 2 in the vitamin V performed efficiently in the presence of tris(triphenylphosphine)rhodium(I) chloride [Wilkinson's catalyst, $(Ph_3P)_3RhCl$]. Such reduction conditions allowed to reduce only $C(2)=CH_2$ unit leaving C(5)-C(8) butadiene moiety unaffected. The isolated material is an epimeric mixture (ca. 1:1) of 2-methyl-19-nor-vitamins Ia and Ib differing in configuration at C-2. The mixture can be used without separation or, if desired, the individual 2α- and 2β-isomers can be separated by an efficient HPLC system.

The overall process of the synthesis of compounds Ia and Ib is illustrated and described more completely in U.S. Pat. No. 5,945,410 entitled "2-Alkyl-19-Nor-Vitamin D Compounds" the specification of which is specifically incorporated herein by reference.

Specifically, the preparation of hydrindanone II is described hereinafter and illustrated in Scheme I. The final steps of the convergent synthesis, i.e. the coupling of this compound with phosphine oxide 7 followed by hydroxyl deprotection in the vitamin D compound 8 and reduction/hydrogenation of the exomethylene unit in 2-methylene-19-nor-vitamin D compound V is also hereinafter described and illustrated in Scheme 2.

Preparation of (20S)-de-A,B-8β-benzoyloxy-20-(hydroxymethyl)pregnane (1).

The starting alcohol 1 was prepared from commercial vitamin $D_2$ in 70% yield, according to the procedure published by J. C. Hanekamp, R. B. Rookhuizen, H. J. T. Bos, L. Brandsma *Tetrahedron*, 1992, 48, 9283–9294.

Ozone was passed through a solution of vitamin $D_2$ (3 g, 7.6 mmol) in methanol (250 mL) and pyridine (2.44 g, 2.5 mL, 31 mmol) for 50 min at −78° C. The reaction mixture was then flushed with an oxygen for 15 min to remove the residual ozone and the solution was treated with $NaBH_4$ (0.75 g, 20 mmol). After 20 min the second portion of $NaBH_4$ (0.75 g, 20 mmol) was added and the mixture was allowed to warm to room temperature. The third portion of $NaBH_4$ (0.75 g, 20 mmol) was then added and the reaction mixture was stirred for 18 h. The reaction was quenched with water (40 mL) and the solution was concentrated under reduced pressure. The residue was extracted with ethyl acetate (3×80 mL) and the combined organic phase was washed with 1M aq. HCl, saturated aq. $NaHCO_3$, dried ($Na_2SO_4$) and concentrated under reduced pressure. The residue was chromatographed on silica gel with hexane/ethyl acetate (75:25) to give (20S)-de-A,B-20-(hydroxymethyl)pregnan-8β-ol (1.21 g, 75% yield) as white crystals.

Benzoyl chloride (2.4 g, 2 mL, 17 mmol) was added to a solution of the 8β,20-diol (1.2 g, 5.7 mmol) and DMAP (30 mg, 0.2 mmol) in anhydrous pyridine (20 mL) at 0° C. The reaction mixture was stirred at 4° C. for 24 h, diluted with methylene chloride (100 mL), washed with 5% aq. HCl, water, saturated aq. $NaHCO_3$, dried ($Na_2SO_4$) and concentrated under reduced pressure. The residue (3.39 g) was treated with solution of KOH (1 g, 15.5 mmol) in anhydrous ethanol (30 mL) at room temperature. After stirring of the reaction mixture for 3 h, ice and 5% aq. HCl were added until pH=6. The solution was extracted with ethyl acetate (3×50 mL) and the combined organic phase was washed with saturated aq. $NaHCO_3$, dried ($Na_2SO_4$) and concentrated under reduced pressure. The residue was chromatographed on silica gel with hexane/ethyl acetate (75:25) to give the alcohol 1 (1.67 g, 93% yield) as a colorless oil: $[\alpha]_D$+56.0 (c 0.48, $CHCl_3$); $^1H$ NMR (400 MHz, $CDCl_3$+TMS) δ 8.08–8.02 (2H, m, o-$H_{Bz}$), 7.59–7.53 (1H, m, p-$H_{Bz}$), 7.50–7.40 (2H, m, m-$H_{Bz}$), 5.42 (1H, d, J=2.4 Hz, 8α-H), 3.65 (1H, dd, J=10.5, 3.2 Hz, 22-H), 3.39 (1H, dd, J=10.5, 6.8 Hz, 22-H), 1.08 (3H, d, J=5.3 Hz, 21-$H_3$), 1.07 (3H, s, 18-$H_3$); $^{13}C$ NMR (125 MHz) δ 166.70 (s, C=O), 132.93 (d, p-$C_{Bz}$), 131.04 (s, i-$C_{Bz}$), 129.75 (d, o-$C_{Bz}$), 128.57 (d, m-$C_{Bz}$), 72.27 (d, C-8), 67.95 (t, C-22), 52.96 (d), 51.60 (d), 42.15 (s, C-13), 39.98 (t), 38.61 (d), 30.73 (t), 26.81 (t), 22.91 (t), 18.20 (t), 16 87 (q, C-21), 13.81 (q, C-18); MS (EI) m/z 316 (5, M$^+$), 301 (3, M$^+$-Me), 299 (1, M$^+$-OH), 298 (2, M$^+$-$H_2O$), 285 (10, M$^+$-$CH_2OH$), 257 (6), 230 (9), 194 (80), 135 (84), 105 (100); exact mass calculated for $C_{20}H_{28}O_3$ 316.2038, found 316.2019.

Preparation of (20S)-de-A,B-8β-benzoyloxy-20-formylpregnane (2).

A mixture of alcohol 1 (1.63 g, 5.2 mmol), pyridinium dichromate (6.05 g, 16.1 mmol) and pyridinium p-toluenesulfonate (100 mg, 0.4 mmol) in anhydrous methylene chloride (30 mL) was stirred at room temperature for 12 h. The resulting suspension was filtered through a short layer of Celite. The adsorbent was washed with ether, solvents were removed under reduced pressure and a residue was purified by column chromatography on silica gel with hexane/ethyl acetate (90:10) to give the aldehyde 2 (1.36 g, 83% yield) as an oil: $^1H$ NMR (400 MHz, $CDCl_3$+TMS) δ 9.60 (1H, d, J=3.1 Hz, CHO), 8.05 (2H, m, o-$H_{Bz}$), 7.57 (1H, m, p-$H_{Bz}$), 7.45 (2H, m, m-$H_{Bz}$), 5.44 (1H, s, 8α-H), 2.39 (1H, m, 20-H), 2.03 (2H, dm, J=11.5 Hz), 1.15 (3H, d, J=6.9 Hz, 21-$H_3$), 1.10 (3H, s, 18-$H_3$); MS (EI) m/z 314 (1, M$^+$), 299 (0.5, M$^+$-Me), 286 (1, M$^+$-CO), 285 (5, M$^+$-CHO), 257 (1, M$^+$-$C_3H_5O$), 209 (10, M$^+$-PhCO), 192 (38), 134 (60), 105 (100), 77 (50); exact mass calculated for $C_{20}H_{26}O_3$ 314.1882, found 314.1887.

Preparation of (20R)-de-A,B-8β-benzoyloxy-20-(hydroxymethyl)pregnane (3).

The aldehyde 2 (1.36 g, 4.3 mmol) was dissolved in $CH_2Cl_2$ (15 mL) and a 40% aq. n-$Bu_4NOH$ solution (5.6 mL, 5.57 g, 8.6 mmol) was added. The resulting mixture was stirred at room temperature for 16 h, diluted with methylene chloride (30 mL), washed with water, dried (Na$_2$SO$_4$) and concentrated under reduced pressure. A residue was chromatographed on silica gel with hexane/ethyl acetate (95:5) to afford a mixture of aldehyde 2 and its 20-epimer (730 mg, 53% yield) in ca. 1:1.7 ratio (by $^1$H NMR).

This mixture of aldehydes (730 mg, 2.3 mmol) was dissolved in THF (5 mL) and NaBH$_4$ (175 mg, 4.6 mmol) was added, followed by a dropwise addition of ethanol (5 mL). The reaction mixture was stirred at room temperature for 30 min and it was quenched with a saturated aq. NH$_4$Cl solution. The mixture was extracted with ether (3×30 mL) and the combined organic phase was washed with with water, dried (Na$_2$SO$_4$) and concentrated under reduced pressure. The residue was chromatographed on silica gel with hexane/ethyl acetate (95:5→80:20) to give the desired, pure (20R)-alcohol 3 (366 mg, 52% yield) as an oil and a mixture of 3 and its 20-epimer 1 (325 mg, 45% yield) in ca. 1:4 ratio (by $^1$H NMR).

3: $[\alpha]_D$ +43.0 (c 0.54, CHCl$_3$); $^1$H NMR (500 MHz, CDCl$_3$+TMS) δ 8.10–8.00 (2H, m, o-H$_{Bz}$), 7.60–7.53 (1H, m, p-H$_{Bz}$), 7.48–7.41 (2H, m, m-H$_{Bz}$), 5.42 (1H, br s, 8α-H), 3.75 (1H, dd, J=10.6, 3.5 Hz, 22-H), 3.48 (1H, dd, J=10.6, 7.0 Hz, 22-H), 1.069 (3H, s, 18-H$_3$), 0.973 (3H, d, J=6.7 Hz, 21-H$_3$); $^{13}$C NMR (125 MHz) δ 166.70 (s, C=O), 132.94 (d, p-C$_{Bz}$), 131.05 (s, i-C$_{Bz}$), 129.76 (d, o-C$_{Bz}$), 128.59 (d, m-C$_{Bz}$), 72.28 (d, C-8), 66.95 (t, C-22), 52.94 (d), 51.77 (d), 41.96 (s, C-13), 39.56 (t), 37.78 (d), 30.75 (t), 26.67 (t), 22.71 (t), 18.25 (t), 16.76 (q, C-21), 14.14 (q, C-18); MS (EI) m/z 316 (16, M$^+$), 301 (5, M$^+$-Me), 299 (2, M$^+$-OH), 298 (3, M$^+$-H$_2$O), 285 (9, M$^+$-CH$_2$OH), 257 (5), 242 (11), 230 (8), 194 (60), 147 (71), 105 (100); exact mass calculated for C$_{20}$H$_{28}$O$_3$ 316.2038, found 316.2050.

Preparation of (20R)-de-A,B-8-benzoyloxy-20-[(p-toluenesulfonyl)oxymethyl]pregnane (4).

To a stirred solution of the alcohol 3 (393 mg, 1.24 mmol), DMAP (10 mg, 0.08 mmol) and Et$_3$N (0.7 mL, 0.51 g, 5.04 mmol) in anhydrous methylene chloride (10 mL) was added p-toluenesulfonyl chloride (320 mg, 1.68 mmol) at 0° C. The reaction mixture was allowed to warm to room temperature (4 h) and stirring was continued for additional 22 h. Methylene chloride (60 mL) was added and the mixture was washed with a saturated aq. NaHCO$_3$ solution, dried (Na$_2$SO$_4$) and concentrated under reduced pressure. A residue was chromatographed on silica gel with hexane/ethyl acetate (95:5) to afford a tosylate 4 (533 mg, 91% yield) as a colorless oil: $[\alpha]_D$=+15.0 (c 0.54, CHCl$_3$); $^1$H NMR (500 MHz, CDCl$_3$+TMS) δ 8.02 (2H, m, o-H$_{Bz}$), 7.80 (2H, d, J=8.2 Hz, o-H$_{Ts}$), 7.55 (1H, m, p-H$_{Bz}$), 7.44 (2H, m, m-H$_{Bz}$), 7.35 (2H, d, J=8.2 Hz, m-H$_{Ts}$), 5.39 (1H, br s, 8α-H), 4.15 (1H, dd, J=9.4, 3.4 Hz, 22-H), 3.83 (1H, dd, J=9.4, 7.1 Hz, 22-H), 2.457 (3H, s, Me$_{Ts}$), 1.98 (1H, m), 0.978 (3H, s, 18-H$_3$), 0.898 (3H, d, J=6.6 Hz, 21-H$_3$); $^{13}$C NMR (125 MHz) δ 166.60 (s, C=O), 144.87 (s, p-C$_{Ts}$), 133.35 (s, i-C$_{Ts}$), 132.98 (d, p-C$_{Bz}$), 130.94 (s, i-C$_{Bz}$), 129.97 (d, m-C$_{Ts}$), 129.72 (d, o-C$_{Bz}$), 128.58 (d, m-C$_{Bz}$), 128.13 (d, m-C$_{Bz}$), 128.13 (d, o-C$_{Ts}$), 74.21 (t, C-22), 72.03 (d, C-8), 52.44 (d), 51.52 (d), 41.82 (s, C-13), 39.30 (t), 35.00 (d), 30.57 (t), 26.56 (t), 22.54 (t), 21.85 (q, Me$_{Ts}$), 18.12 (t), 16.85 (q, C-21), 14.09 (q, C-18); MS (EI) m/z 470 (1, M$^+$), 365 (33, M$^+$-PhCO), 348 (64, M$^+$-PhCOOH), 193 (52), 176 (71), 134 (72), 105 (100); exact mass calculated for C$_{27}$H$_{34}$O$_5$S 470.2127, found 470.2091.

Preparation of (20S)-de-A,B-cholestan-8β-ol (6).

Magnesium turnings (1.32 g, 55 mmol), 1-chloro-3-methylbutane (3.3 mL, 2.9 g, 27.2 mmol) and iodine (2 crystals) were refluxed in anhydrous THF (18 mL) for 10 h. The solution of the formed Grignard reagent 5 was cooled to −78° C. and added dropwise via cannula to a solution of the tosylate 4 (348 mg, 0.74 mmol) in anhydrous THF (5 mL) at −78° C. Then 6 mL of the solution of Li$_2$CuCl$_4$ [prepared by dissolving of a dry LiCl (232 mg, 5.46 mmol) and dry CuCl$_2$ (368 mg, 2.75 mmol) in anhydrous THF (27 mL)] was added dropwise via cannula to the reaction mixture at −78° C. The cooling bath was removed and the mixture was stirred at room temperature for 20 h and then poured into 1M aq. H$_2$SO$_4$ solution (25 mL) containing ice (ca. 100 g). The mixture was extracted with methylene chloride (3×50 mL) and the combined organic layers were washed with saturated aq. NH$_4$Cl, saturated aq. NaHCO$_3$, dried (Na$_2$SO$_4$) and concentrated under reduced pressure. The residue was chromatographed on silica gel with chloroform to give alcohol 6 (149 mg, 76% yield) as a colorless oil: $^1$H NMR (400 MHz, CDCl$_3$+TMS) δ 4.07 (1H, d, J=2.2 Hz, 8α-H), 1.98 (1H, dm, J=13.1 Hz), 0.93 (3H, s, 18-H$_3$), 0.86 (6H, d, J=6.6 Hz, 26- and 27-H$_3$), 0.81 (3H, d, J=6.6 Hz, 21-H$_3$); $^{13}$C NMR (125 MHz) δ 69.41 (d, C-8), 56.27 (d), 52.62 (d), 41.84 (s, C-13), 40.28 (t), 39.38 (t), 35.40 (t), 34.83 (d), 33.51 (t), 28.03 (d), 27.10 (t), 23.93 (t), 22.72 (q, C-26/27), 22.63 (q, C-26/27), 22.40 (t), 18.53 (q, C-21), 17.47 (t), 13.73 (q, C-18); MS (EI) m/z 266 (7, M$^+$), 251 (6, M$^+$-Me), 248 (2, M$^+$-H$_2$O), 233 (4, M$^+$-Me-H$_2$O), 163 (6), 152 (11), 135 (38), 111 (100); exact mass calculated for C$_{18}$H$_{34}$O 266.2610, found 266.2601.

Preparation of (20S)-de-A,B-cholestan-8-one (II).

Pyridinium dichromate (90 mg, 239 μmol) was added to a solution of the alcohol 6 (15 mg, 56 μmol) and pyridinium p-toluenesulfonate (2 mg, 8 μmol) in anhydrous methylene chloride (6 mL). The resulting suspension was stirred at room temperature for 3.5 h. The reaction mixture was filtered through a Waters silica Sep-Pak cartridge (2 g) that was further washed with CHCl$_3$. After removal of solvents ketone II (13 mg, 88% yield) was obtained as a colorless oil: $^1$H NMR (400 MHz, CDCl$_3$+TMS) δ 2.46 (1H, dd, J=11.5, 7.6 Hz), 0.89 (6H, d, J=6.6 Hz, 26- and 27-H$_3$), 0.87 (3H, d, J=6.1 Hz, 21-H$_3$), 0.65 (3H, s, 18-H$_3$); MS (EI) m/z 264 (41, M$^+$), 249 (37, M$^+$-Me), 246 (3, M$^+$-H$_2$O), 231 (3, M$^+$-Me-H$_2$O), 221 (50, M$^+$-C$_3$H$_7$), 152 (34), 125 (100), 111 (69); exact mass calculated for C$_{18}$H$_{32}$O 264.2453, found 264.2454.

Preparation of (20S)-1α-hydroxy-2-methylene-19-norvitamin D$_3$ (V).

To a solution of phosphine oxide 7 (34 mg, 58 μmol) in anhydrous THF (450 μL) at −20° C. was slowly added PhLi (1.7 M in cyclohexane-ether, 75 μL, 128 μmol) under argon with stirring. The solution turned deep orange. After 30 min the mixture was cooled to −78° C. and a precooled (−78° C.) solution of ketone II (12 mg, 45 μmol) in anhydrous THF (200+100 μL) was slowly added. The mixture was stirred under argon at −78° C. for 3 h and at 0° C. for 18 h. Ethyl acetate was added, and the organic phase was washed with brine, dried (Na$_2$SO$_4$) and evaporated. The residue was dissolved in hexane and applied on a Waters silica Sep-Pak cartridge (2 g). The cartridge was washed with hexane and hexane/ethyl acetate (99.5:0.5) to give 19-norvitamin derivative 8 (12 mg). The Sep-Pak was then washed with hexane/ethyl acetate (96:4) to recover the unchanged C,D-ring ketone II (7 mg), and with ethyl acetate to recover diphenylphosphine oxide 7 (19 mg). The protected vitamin 8 was further purified by HPLC (10×250 mm Zorbax-Silica column, 4 mL/min) using hexane/2-propanol (99.9:0.1) solvent system. Pure compound 8 (10 mg, 36% yield) was eluted at R$_v$=15 mL as a colorless oil: UV (in hexane) λ$_{max}$ 262.5, 252.5, 243.5 nm; $^1$H NMR (500 MHz, CDCl$_3$) δ 6.21 and 5.82 (1H and 1H, each d, J=11.1 Hz, 6- and 7-H), 4.95 and 4.90 (1H and 1H, each s, =CH$_2$), 4.41 (2H, m, 1β- and 3α-H), 2.80 (1H, dd, J=11.9, 3.5 Hz, 9β-H), 2.49 (1H, dd, J=13.2, 6.0 Hz, 10α-H), 2.44 (1H, dd, J=12.7, 4.6 Hz, 4α-H), 2.32 (1H, dd, J=13.2, 3.1 Hz, 10β-H), 2.16 (1H, dd, J=12.7, 8.2 Hz, 4β-H), 1.98 (2H, m), 1.84 (1H, m), 0.876 (9H, s, Si-t-Bu), 0.851 (6H, d, J=6.0 Hz, 26- and 27-H$_3$), 0.845 (9H, s, Si-t-Bu), 0.820 (3H, d, J=6.5 Hz, 21-H$_3$), 0.521 (3H, s, 18-H$_3$), 0.060, 0.046, 0.029 and 0.006 (each 3H, each s, 4×Si—CH$_3$); MS (EI) m/z 628 (3, M$^+$), 613 (1, M$^+$-Me), 571 (3, M$^+$-t-Bu), 496 (63, M$^+$-t-BuMe$_2$SiOH), 383 (4, M$^+$-t-BuMe$_2$SiOH—C$_8$H$_{17}$), 366 (21), 234 (20), 129 (41), 75 (100); exact mass calculated for C$_{39}$H$_{72}$O$_2$Si$_2$ 628.5071, found 628.5068.

Protected vitamin 8 (10 mg, 16 μmol) was dissolved in anhydrous THF (3 mL) and a solution of tetrabutylammonium fluoride (1 M in THF, 160 μL, 160 μmol) was added, followed by freshly activated molecular sieves 4A (300 mg). The mixture was stirred under argon at room temperature for 2 h, then diluted with 2 mL of hexane/ethyl acetate (6:4) and applied on a Waters silica Sep-Pak cartridge (2 g). Elution with the same solvent system gave the crude product V that was further purified by HPLC (10×250 mm Zorbax-Silica column, 4 mL/min) using hexane/2-propanol (9:1) solvent system. Analytically pure 2-methylene-19-norvitamin V (3.3 mg, 52% yield) was collected at R$_v$=32 mL as a colorless oil: UV (in EtOH) λ$_{max}$ 261.5, 251.5, 243.5 nm; $^1$H NMR (500 MHz, CDCl$_3$+TMS) δ 56.36 and 5.88 (1H and 1H, each d, J=11.3 Hz, 6- and 7-H), 5.11 and 5.09 (each 1H, each s, =CH$_2$), 4.47 (2H, m, 1β- and 3α-H), 2.85 (1H, dd, J=13.4, 4.6 Hz, 10β-H), 2.81 (1H, br d, J=13.9 Hz, 9β-H), 2.58 (1H, dd, J=13.2, 3.7 Hz, 4α-H), 2.33 (1H, dd, J=13.2, 6.1 Hz, 4β-H), 2.29 (1H, dd, J=13.4, 8.4 Hz, 10α-H), 1.99 (2H, m), 1.86 (1H, m), 0.867 (6H, d, J=6.6 Hz, 26- and 27-H$_3$), 0.839 (3H, d, J=6.5 Hz, 21-H$_3$), 0.547 (3H, s, 18-H$_3$); MS (EI) m/z 400 (100, M$^+$), 385 (5, M$^+$-Me), 382 (16, M$^+$-H$_2$O), 367 (6, M$^+$-Me-H$_2$O), 349 (3, M$^+$-Me-2H$_2$O), 315 (46), 287 (56, M$^+$-C$_8$H$_{17}$), 269 (52), 247 (42); exact mass calculated for C$_{27}$H$_4$O$_2$ 400.3341, found 400.3346.

Preparation of (20S)-1α-hydroxy-2α-methyl-19-norvitamin D$_3$ (Ia) and (20S)-1α-hydroxy-2β-methyl-19-norvitamin D$_3$ (Ib).

Tris(triphenylphosphine)rhodium (I) chloride (3.5 mg, 3.8 μmol) was added to dry benzene (2.5 mL) presaturated with hydrogen. The mixture was stirred at room temperature until a homogeneous solution was formed (ca. 45 min). A solution of vitamin V (1.8 mg, 4.5 μmol) in dry benzene (400+400 μL) was then added and the reaction was allowed to proceed under a continuous stream of hydrogen for 3 h. Benzene was removed under vacuum, the residue was redissolved in hexane/ethyl acetate (1:1) and applied on a Waters silica Sep-Pak cartridge (2 g). A mixture of 2-methyl vitamins was eluted with the same solvent system. The compounds were further purified by HPLC (10×250 mm Zorbax-Silica column, 4 mL/min) using hexane/2-propanol (9:1) solvent system. The mixture of 2-methyl-19-norvitamins Ia and Ib gave a single peak at R$_v$=34 mL. Separation of both epimers was achieved by reversed-phase HPLC (10×250 mm Chromegabond C18 column, 3 mL/min) using methanol/water (9:1) solvent system. 2β-Methyl vitamin Ib (280 μg, 15% yield) was collected at R$_v$=47 mL and its 2α-epimer Ia (382 μg, 21% yield) at R$_v$=51 mL.

Ia: UV (in EtOH) λ$_{max}$ 260.5, 250.5, 242.5 nm; $^1$H NMR (500 MHz, CDCl$_3$+TMS) δ 6.37 and 5.82 (1H and 1H, each d, J=11.1 Hz, 6- and 7-H), 3.96 (1H, m, w/2=14 Hz, 1β-H), 3.61 (1H, m, w/2=20 Hz, 3α-H), 2.80 (2H, br m, 9β- and 10α-H), 2.60 (1H, dd, J=13.0, 4.5 Hz, 4α-H), 2.22 (1H, br d, J=12.8 Hz, 10β-H), 2.13(1H, ~t, J=13.0 Hz, 4β-H), 1.133 (3H, d, J=6.8 Hz, 2α-CH$_3$), 0.866 (6H, d, J=6.6 Hz, 26- and 27-H$_3$), 0.833 (3H, d, J=6.4 Hz, 21-H$_3$), 0.530 (3H, s, 18-H$_3$); MS (EI) m/z 402 (100, M$^+$), 387 (4, M$^+$-Me), 384 (7, M$^+$-H$_2$O), 369 (3, M$^+$-Me-H$_2$O), 317 (24), 289 (60, M$^+$-C$_8$H$_{17}$), 271 (33), 259 (40), 247 (63); exact mass calculated for C$_{27}$H$_{46}$O$_2$ 402.3498, found 402.3496.

Ib: UV (in EtOH) λ$_{max}$ 260.5, 250.0, 242.0 nm; $^1$H NMR (500 MHz, CDCl$_3$+TMS) δ 6.26 and 5.87 (1H and 1H, each d, J=11.3 Hz, 6-H and 7-H), 3.90 (1H, m, w/2=14 Hz, 3α-H), 3.50 (1H, m, w/2=26 Hz, 1β-H), 3.08 (1H, dd, J=12.6, 4.3 Hz, 10β-H), 2.80 (1H, dd, J=12.5, 3.8 Hz, 9β-H), 2.43 (1H, br d, J=ca. 14 Hz, 4α-H), 2.34 (1H, dd, J=13.9, 3.0 Hz, 4β-H), 1.143 (3H, d, J=6.8 Hz, 2β-CH$_3$) 0.867 (6H, d, J=6.6 Hz, 26- and 27-H$_3$), 0.839 (3H, d, J=6.5 Hz, 21-H$_3$), 0.543 (3H, s, 18-H$_3$); MS (EI) m/z 402 (100, M$^+$), 387 (8, M$^+$-Me), 384 (8, M$^+$-H$_2$O), 369 (5, M$^+$-Me-H$_2$O), 317 (42), 289 (88, M$^+$-C$_8$H$_{17}$), 271 (52), 259 (55), 247 (66); exact mass calculated for C$_{27}$H$_{46}$O$_2$ 402.3498, found 402.3486.

Scheme 1

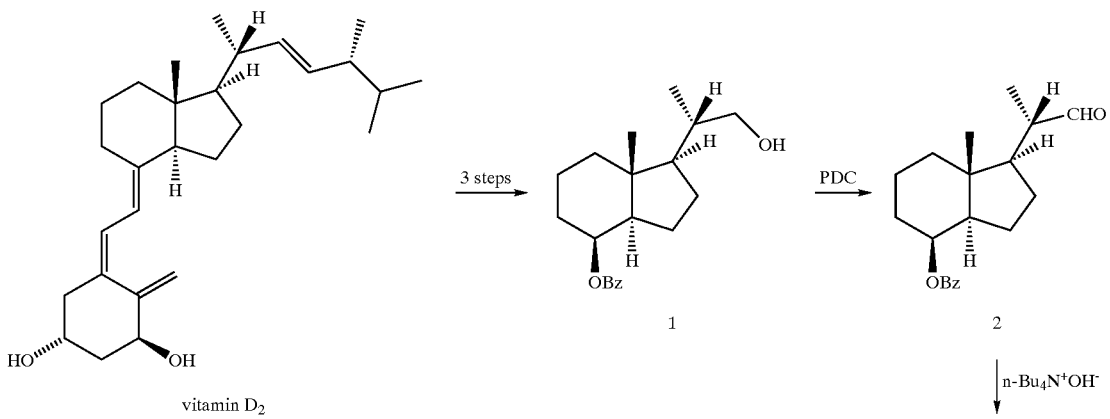

-continued
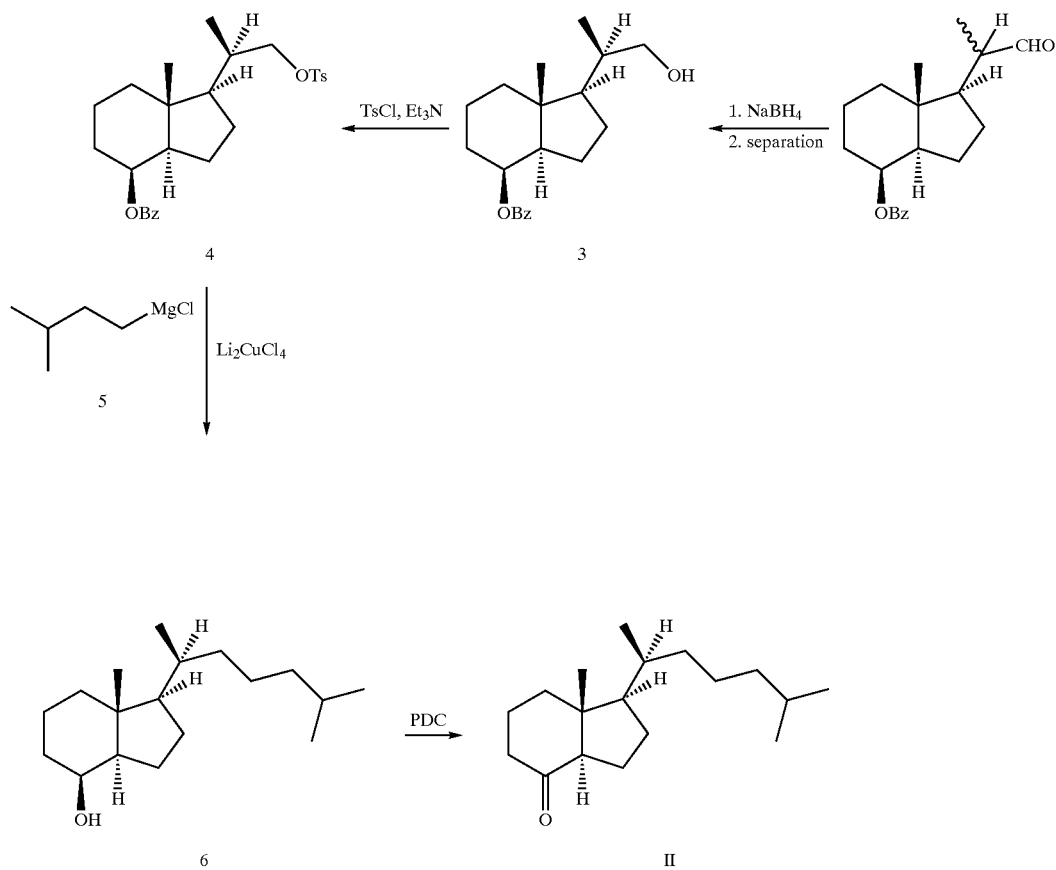
Scheme 2
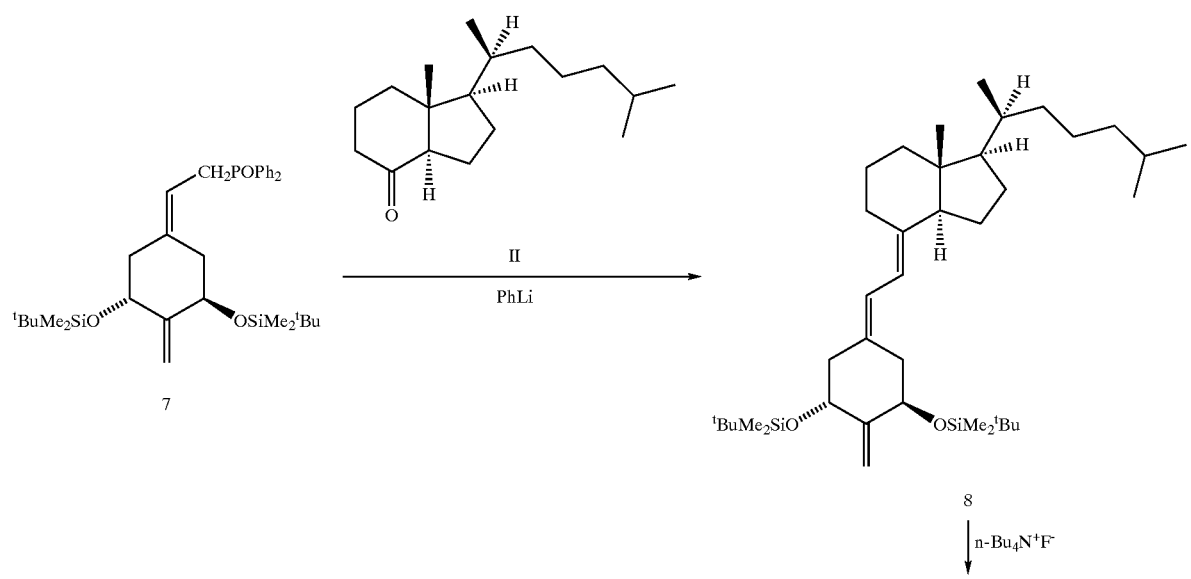

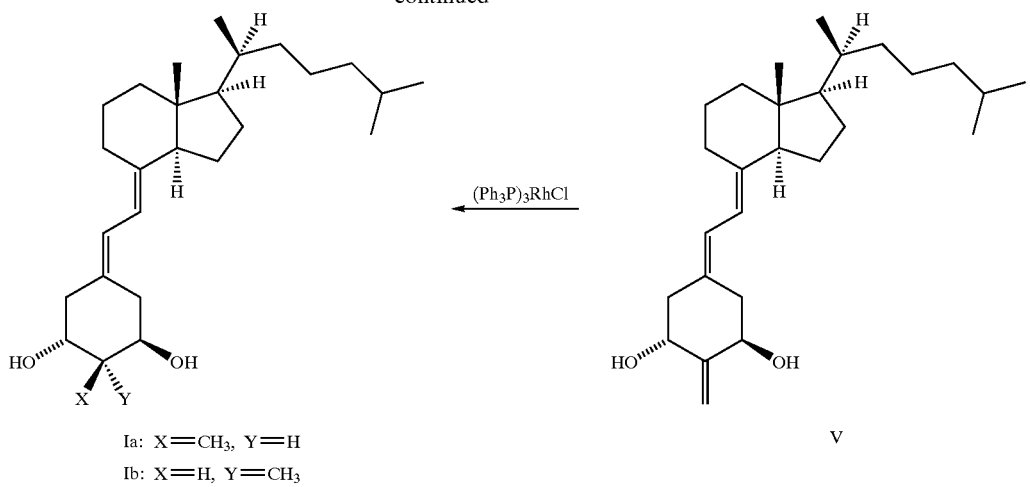

Ia: X=CH₃, Y=H
Ib: X=H, Y=CH₃

V

Biological Activity of (20S)-1α-Hydroxy-2α-methyl and 2β-Methyl-19-nor-vitamin $D_3$ The 2β-methyl-(20S)-1α-hydroxyvitamin $D_3$ does not bind to the vitamin D receptor, while the 2α-methyl-(20S)-1α-hydroxyvitamin $D_3$ binds the receptor but at a 100-fold less affinity than 1α,25-dihydroxyvitamin $D_3$ (1,25-(OH)$_2D_3$) (FIG. 1). The absence of a 25-hydroxyl group in these compounds is largely responsible (see Eisman, J. A. and H. F. DeLuca, Steroids 30, 245–257, 1977) for this diminished activity. Importantly, the 2α-methyl derivative is superior to the 2β-methyl analog in binding to the receptor.

Figure 2:
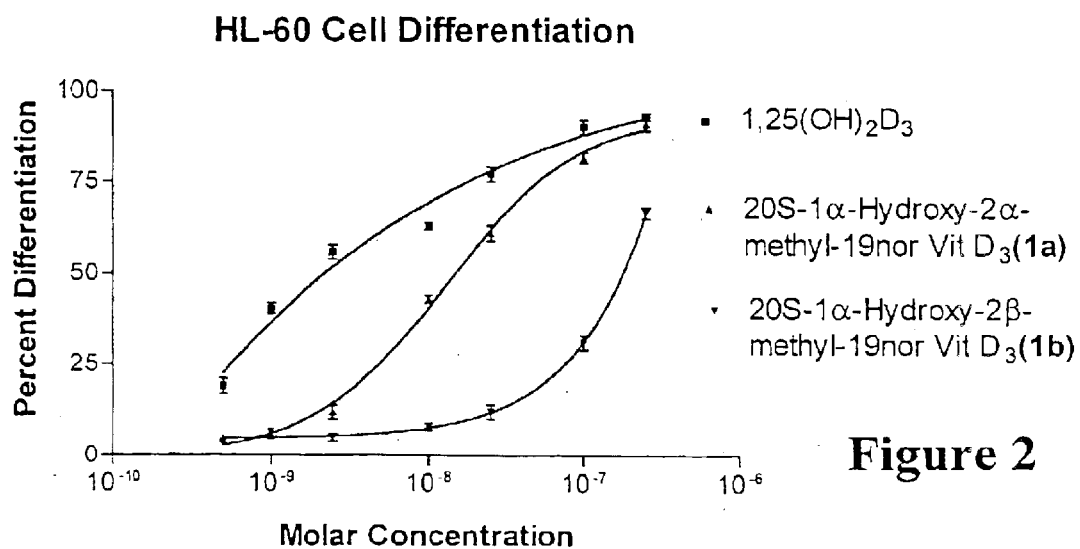
FIG. 2 is a graph illustrating the percent HL-60 cell differentiation as a function of the concentration of (20S)-1α-hydroxy-2β-methyl-19-nor-vitamin $D_3$, (20S)-1α-hydroxy-2β-methyl-19-nor-vitamin $D_3$, and of 1α,25-dihydroxyvitamin $D_3$.

Surprisingly, FIG. 2 illustrates (20S)-1α-hydroxy-2α-methyl-19-nor-vitamin $D_3$ is almost as potent as 1,25-(OH)$_2D_3$ on HL-60 differentiation, making it an excellent candidate for the treatment of psoriasis and cancer, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin. The 2β derivative is 100 times less active than 1,25(OH)$_2D_3$ making it less effective in these areas.

The data in Table 1 show that (20S)-1α-hydroxy-2α-methyl-19-nor-vitamin $D_3$ has high activity relative to that of 1,25-(OH)$_2D_3$, the natural hormone, in stimulating intestinal calcium transport. Also, (20S)-1α-hydroxy-2β-methyl-19-nor-vitamin $D_3$ has significant activity in stimulating intestinal calcium transport, and its activity is about the same as 1,25-(OH)$_2D_3$.

The data in Table 1 also demonstrate that (20S)-1α-hydroxy-2α-methyl-19-nor-vitamin $D_3$ has higher bone calcium mobilization activity, as compared to 1,25-(OH)$_2D_3$. Also, (20S)-1α-hydroxy-2β-methyl-19-nor-vitamin $D_3$ has significant bone calcium mobilization activity, and its activity is about the same as 1,25-(OH)$_2D_3$.

A very important feature of these analogs is that they bind poorly or not at all to the vitamin D receptor, while having biological activity either higher than or equal to 1,25-(OH)$_2D_3$. This suggests that these analogs are pro drugs. That is, they are probably activated in vivo by being 25-hydroxylated. Once 25-hydroxylated, they are then able to bind the vitamin D receptor and provide activity. These results suggest that these compounds might be preferable to the final drug in that they are slowly activated within the body providing a more controlled and prolonged activity.

The data in Table 1 thus illustrate that (20S)-1α-hydroxy-2α-methyl-19-nor-vitamin $D_3$ may be characterized as having significant and very potent calcemic activity which is greater than 1,25-(OH)$_2D_3$, and that (20S)-1α-hydroxy-2β-methyl-19-nor-vitamin $D_3$ also has significant and very potent calcemic activity that is about the same as 1,25-(OH)$_2D_3$.

Competitive binding of the analogs to the porcine intestinal receptor was carried out by the method described by Dame et al. (Biochemistry 25, 4523–4534, 1986).

The differentation of HL-60 promyelocytic into monoctyes was determined as described by Ostrem et al. (J. Boil. Chem. 262, 14164–14171, 1987).

Intestinal calcium transport was determined as described by Perlman et al. (Biochemistry 29, 190–196, 1990).

Interpretation of Data

The in vivo tests to determine serum calcium of rats on a low calcium diet provides an insight to osteoblastic or bone activity of (20S)-1α-hydroxy-2α-methyl-19-nor-vitamin $D_3$ and (20S)-1α-hydroxy-2β-methyl-19-nor-vitamin $D_3$. The data in Table 1 show that (20S)-1α-hydroxy-2α-methyl-19-nor-vitamin $D_3$ is significantly more potent than 1,25(OH)$_2D_3$ in raising calcium in the plasma via the stimulation of the osteoblasts. At the same time, the activity of (20S)-1α-hydroxy-2α-methyl-19-nor-vitamin $D_3$ on intestinal calcium transport is also significantly greater than that of 1,25-(OH)$_2D_3$ (Table 1). Therefore, these data show (20S)-1α-hydroxy-2α-methyl-19-nor-vitamin $D_3$ to have significant and very potent activity on bone which is higher than 1,25(OH)$_2D_3$.

The data in Table 1 also show that (20S)-1α-hydroxy-2β-methyl-19-nor-vitamin $D_3$ is only slightly less potent than 1,25(OH)$_2D_3$ in raising calcium in the plasma calcium via the stimulation of the osteoblasts. At the same time, the activity of (20S)-1α-hydroxy-2β-methyl-19-nor-vitamin $D_3$ on intestinal calcium transport is about the same as that of 1,25-(OH)$_2D_3$ (Table 1). Therefore, these data show (20S)-1α-hydroxy-2β-methyl-19-nor-vitamin $D_3$ to have significant and very potent activity on bone about equal to 1,25(OH)$_2D_3$.

The compounds Ia and Ib exhibit a desired, and highly advantageous, pattern of biological activity. These compounds are characterized by relatively high intestinal calcium transport activity, as compared to that of 1α,25-dihydroxyvitamin $D_3$, while also exhibiting relatively high activity, as compared to 1α,25-dihydroxyvitamin $D_3$, in their ability to mobilize calcium from bone. Hence, these compounds are highly specific in their calcemic activity. Their activity on mobilizing calcium from bone and either high or normal intestinal calcium transport activity allows the in vivo administration of these compounds for the treatment of metabolic bone diseases where bone loss is a major concern. Because of their calcemic activity on bone, these compounds would be preferred therapeutic agents for the treatment of diseases where bone formation is desired, such as osteoporosis, especially low bone turnover osteoporosis, steroid induced osteoporosis, senile osteoporosis or post-menopausal osteoporosis, as well as osteomalacia.

(20S)-1α-Hydroxy-2α-methyl-19-nor-vitamin $D_3$ and (20S)-1α-hydroxy-2β-methyl-19-nor-vitamin $D_3$ are much less active than 1,25$(OH)_2D_3$ in binding to the vitamin D receptor (FIG. 1), and they are both also only slightly less active than 1,25-$(OH)_2D_3$ in causing differentiation of the promyelocyte, HL-60, into the monocyte (FIG. 2). This result suggests that both (20S)-1α-hydroxy-2α-methyl-19-nor-vitamin $D_3$ and (20S)-1α-hydroxy-2β-methyl-19-nor-vitamin $D_3$ will be very effective in psoriasis because they have direct cellular activity in causing cell differentiation and in suppressing cell growth. It also indicates that they both will have significant activity as an anti-cancer agent, especially against leukemia, colon cancer, breast cancer and prostate cancer, as well as against skin conditions such as dry skin (lack of dermal hydration), undue skin slackness (insufficient skin firmness), insufficient sebum secretion and wrinkles. These results also illustrate that (20S)-1α-hydroxy-2α-methyl-19-nor-vitamin $D_3$ and (20S)-1α-hydroxy-2β-methyl-19-nor-vitamin $D_3$ are both excellent candidates for numerous human therapies and that they may be useful in a number of circumstances in addition to cancer and psoriasis such as autoimmune diseases.

Male, weanling Sprague-Dawley rats were placed on Diet 11 (0.47% Ca) diet+AEK for 11 days, followed by Diet 11 (0.02% Ca)+AEK for 31 days. Dosing (i.p.) began 7 days prior to sacrifice. Doses were given on a daily basis, 24 hours apart. The first 10 cm of the intestine was collected for gut transport studies and serum was collected for bone Ca mobilization analysis. The results are reported in Table 1.

TABLE 1

Response of Intestinal Calcium Transport and Serum Calcium (Bone Calcium Mobilization) Activity to Chronic Doses of 1,25-$(OH)_2D_3$ and (20S)-1α-Hydroxy-2α-methyl-19-nor-vitamin $D_3$ and (20S)-1α-Hydroxy-2β-methyl-19-nor-vitamin $D_3$

| Compound | Amount (pmol/day) | Ca transport S/M (mean ± SEM) | Serum Ca (mean ± SEM) |
| --- | --- | --- | --- |
| none (control) | 0 | 4.5 ± 0.40 | 4.4 ± 0.07 |
| 1α,25-$(OH)_2D_3$ | 130 | 5.3 ± 0.42 | 5.0 ± 0.05 |
|  | 260 | 6.5 ± 0.84 | 5.5 ± 0.16 |
| (20S)-1α-(OH)-2α-methyl-19-nor-$D_3$ | 130 | 8.6 ± 0.90 | 10.0 ± 0.20 |
|  | 260 | 6.7 ± 0.68 | 12.7 ± 0.15 |
| (20S)-1α-(OH)-2β-methyl-19-nor-$D_3$ | 130 | 6.8 ± 0.73 | 4.8 ± 0.04 |
|  | 260 | 5.7 ± 0.45 | 5.1 ± 0.04 |

*The above data are the average and standard error (SE) from 5 animals.

For treatment purposes, the compounds of this invention defined by formula Ia and Ib may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 μg to 100 μg per day of the compounds are appropriate for treatment purposes, such doses being adjusted according to the disease to be treated, its severity and the response of the subject as is well understood in the art. Since the compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the (20S)-1α-hydroxy-2α-methyl-19-nor-vitamin $D_3$ or (20S)-1α-hydroxy-2β-methyl-19-nor-vitamin $D_3$ as defined by the above formula Ia and Ib as the active ingredient, and a suitable carrier. An effective amount of such compound for use in accordance with this invention is from about 0.01 μg to about 100 μg per gm of composition, and may be administered topically, transdermally, orally or parenterally in dosages of from about 0.01 μg/day to about 100 μg/day.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100 μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of treating an inflammatory disease selected from the group consisting of rheumatoid arthritis, asthma, and inflammatory bowel diseases, comprising administering to a patient with said disease an effective amount of (20S)-1α-hydroxy-2α-methyl-19-nor-vitamin $D_3$ having the formula:

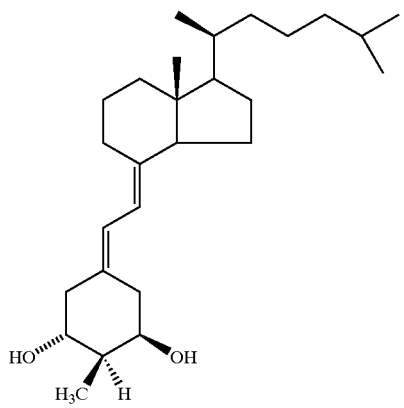

2. The method of claim 1 wherein (20S)-1α-hydroxy-2α-methyl-19-nor-vitamin $D_3$ is administered orally.

3. The method of claim 1 wherein (20S)-1α-hydroxy-2α-methyl-19-nor-vitamin $D_3$ is administered parenterally.

4. The method of claim 1 wherein (20S)-1α-hydroxy-2α-methyl-19-nor-vitamin $D_3$ is administered transdermally.

5. The method of claim 1 wherein (20S)-1α-hydroxy-2α-methyl-19-nor-vitamin $D_3$ is administered in a dosage of from about 0.01 μg/day to about 100 μg/day.

* * * * *